(12) United States Patent
Maheshwari et al.

(10) Patent No.: US 11,471,578 B2
(45) Date of Patent: Oct. 18, 2022

(54) TECHNIQUES FOR REMOVING BOUND TARGET SUBSTANCES DURING DIALYSIS

(71) Applicant: Fresenius Medical Care Holdings, Inc., Waltham, MA (US)

(72) Inventors: Vaibhav Maheshwari, Jersey City, NJ (US); Peter Kotanko, New York, NY (US)

(73) Assignee: FRESENIUS MEDICAL CARE HOLDINGS, INC., Waltham, MA (US)

( * ) Notice: Subject to any disclaimer, the term of this patent is extended or adjusted under 35 U.S.C. 154(b) by 772 days.

(21) Appl. No.: 16/388,248

(22) Filed: Apr. 18, 2019

(65) Prior Publication Data

US 2019/0321537 A1    Oct. 24, 2019

Related U.S. Application Data

(60) Provisional application No. 62/660,101, filed on Apr. 19, 2018.

(51) Int. Cl.
*A61M 1/34*    (2006.01)
*A61M 1/16*    (2006.01)
(Continued)

(52) U.S. Cl.
CPC ........ *A61M 1/3406* (2014.02); *A61M 1/1601* (2014.02); *A61M 1/1603* (2014.02);
(Continued)

(58) Field of Classification Search
CPC .. A61M 1/3406; A61M 1/342; A61M 1/3424; A61M 1/3441; A61M 1/3455; A61M 1/3458; A61M 1/3493; A61M 1/1601; A61M 1/1603; A61M 1/1613; A61M 1/1654; A61M 1/1676; A61M 1/287; A61M 5/142; A61M 2205/52; G06F 9/30; G06F 9/30003; G06F 15/16; G06F 15/163; G06F 15/167; G06F 17/11
See application file for complete search history.

(56) References Cited

U.S. PATENT DOCUMENTS 8,206,591 B2    6/2012    Kotanko et al.

OTHER PUBLICATIONS

Mowry et al., (2015) "2014 Annual Report of the American Association of Poison Control Centers' National Poison Data System (NPDS): 32nd Annual Report", Clinical Toxicology, 53:10, 962-1147, DOI:10.3109/15563650.2015.1102927.

(Continued)

*Primary Examiner* — John Kim
(74) *Attorney, Agent, or Firm* — KDB

(57) ABSTRACT

Systems, methods, and/or apparatuses may be operative to perform a dialysis process that includes a displacer infusion process. The dialysis machine may include at least one processor and a memory coupled to the at least one processor, the memory comprising instructions that, when executed by the processor, may cause the at least one processor to access dialysis information for a dialysis process performed by a dialysis machine, the dialysis information indicating a target substance to be displaced from a binding compound by a displacer, and determine an infusion profile for infusing the displacer into a patient during a displacer infusion process of the dialysis process, the infusion profile determined based on the dialysis information and an infusion constraint. Other embodiments are described.

10 Claims, 9 Drawing Sheets

(51) Int. Cl.
*A61M 5/142* (2006.01)
*G06F 15/16* (2006.01)
*G06F 9/30* (2018.01)
*G06F 17/11* (2006.01)
*G06F 15/167* (2006.01)
*G06F 15/163* (2006.01)
*A61M 1/28* (2006.01)

(52) U.S. Cl.
CPC ........ *A61M 1/1613* (2014.02); *A61M 1/1654* (2013.01); *A61M 1/342* (2013.01); *A61M 1/3424* (2014.02); *A61M 1/3441* (2013.01); *A61M 1/3455* (2013.01); *A61M 1/3458* (2014.02); *A61M 1/3493* (2014.02); *A61M 5/142* (2013.01); *G06F 9/30* (2013.01); *G06F 9/30003* (2013.01); *G06F 15/16* (2013.01); *G06F 15/163* (2013.01); *G06F 15/167* (2013.01); *G06F 17/11* (2013.01); *A61M 1/1676* (2014.02); *A61M 1/287* (2013.01); *A61M 2205/52* (2013.01)

(56) References Cited

OTHER PUBLICATIONS

Deb et al., (2002). A fast and elitist multiobjective genetic algorithm: NSGA-II. Evolutionary Computation, IEEE Transactions on 6. 182-197. 10.1109/4235.996017.

TECHNIQUES FOR REMOVING BOUND TARGET SUBSTANCES DURING DIALYSIS

CROSS-REFERENCE TO RELATED APPLICATION

This application claims priority to U.S. Provisional Patent Application Ser. No. 62/660,101, filed on Apr. 19, 2018, entitled "Toxin Displacer Optimization in Dialysis Treatments," the contents of which are incorporated herein by reference in their entirety.

FIELD

The disclosure generally relates to a dialysis system, and, more particularly, to techniques for removing target substances from the blood of a patient using a displacer compound during dialysis treatment.

BACKGROUND

Dialysis machines are known for use in the treatment of renal disease. The two principal dialysis methods are hemodialysis (HD) and peritoneal dialysis (PD). Various unwanted substances may be removed from a patient's blood during a dialysis treatment, including waste products (for instance, urea), toxins, and foreign substances (for instance, prescription drug molecules). In contrast to free or unbound substances, dialysis processes may not be able to effectively remove protein-bound substances because only the unbound fraction of the substance may pass through the membrane of a dialyzer. Accordingly, protein-bound substances typically require specific treatment methods to be efficiently and effectively removed from the blood of a patient during a dialysis treatment. It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

In accordance with various aspects of the described embodiments is an apparatus that may include a memory and at least one processor coupled to the memory. The memory may include instructions that, when executed by the at least one processor, cause the at least one processor to access dialysis information for a dialysis process performed by a dialysis machine, the dialysis information indicating a target substance to be displaced from a binding compound by a displacer, and determine an infusion profile for infusing the displacer into a patient during a displacer infusion process of the dialysis process, the infusion profile determined based on the dialysis information and an infusion constraint.

In exemplary embodiments of the apparatus, the instructions, when executed by the at least one processor, may cause the at least one processor to perform the displacer infusion process via the dialysis machine by infusing the patient with the displacer according to the infusion profile. In various embodiments of the apparatus, the infusion constraint may include maintaining a concentration of the target substance at or below an initial concentration during the displacer infusion process. In exemplary embodiments of the apparatus, the target substance may include a drug compound and the binding compound may comprise a protein. In various embodiments of the apparatus, the target substance may include phenytoin and the binding compound may comprise albumin. In some embodiments of the apparatus, the displacer may include aspirin.

In various embodiments of the apparatus, the instructions, when executed by the at least one processor, may cause the at least one processor to determine the infusion profile based on a multi-objective optimization (MOO). In some embodiments of the apparatus, the MOO may be determined based on a first objective and a second objective. The first objective may include minimizing the target substance at a completion of the dialysis process in a minimum amount of time. The second objective may comprise the infusion constraint, and the infusion constraint may include maintaining a concentration of the target substance at or below an initial concentration during the displacer infusion process. In various embodiments of the apparatus, the MOO may include a non-dominated sorting genetic algorithm (NSGA).

In exemplary embodiments of the apparatus, the infusion profile may include modifying a flow rate of the displacer into the patient over an infusion time period to satisfy the infusion constraint.

In accordance with various aspects of the described embodiments is a method that may include accessing dialysis information for a dialysis process performed by a dialysis machine, the dialysis information indicating a target substance to be displaced from a binding compound by a displacer, and determining an infusion profile for infusing the displacer into a patient during a displacer infusion process of the dialysis process, the infusion profile determined based on the dialysis information and an infusion constraint.

In some embodiments of the method, the method may include performing the displacer infusion process via the dialysis machine by infusing the patient with the displacer according to the infusion profile. In various embodiments of the method, the infusion constraint may include maintaining a concentration of the target substance at or below an initial concentration during the displacer infusion process. In exemplary embodiments of the method, the target substance may include a drug compound and the binding compound may comprise a protein. In various embodiments of the method, the target substance may include phenytoin and the binding compound may comprise albumin. In some embodiments of the method, the displacer may include aspirin.

In various embodiments of the method, the method may include determining the infusion profile based on a multi-objective optimization (MOO). In some embodiments of the method, the MOO may be determined based on a first objective and a second objective. The first objective may include minimizing the target substance at a completion of the dialysis process in a minimum amount of time. The second objective may comprise the infusion constraint, and the infusion constraint may comprise maintaining a concentration of the target substance at or below an initial concentration during the displacer infusion process. In various embodiments of the method, the MOO may include a non-dominated sorting genetic algorithm (NSGA).

In exemplary embodiments of the method, the infusion profile may include modifying a flow rate of the displacer into the patient over an infusion time period to satisfy the infusion constraint.

BRIEF DESCRIPTION OF THE DRAWINGS

By way of example, specific embodiments of the disclosed machine will now be described, with reference to the accompanying drawings, in which.

DETAILED DESCRIPTION

Figure 1:
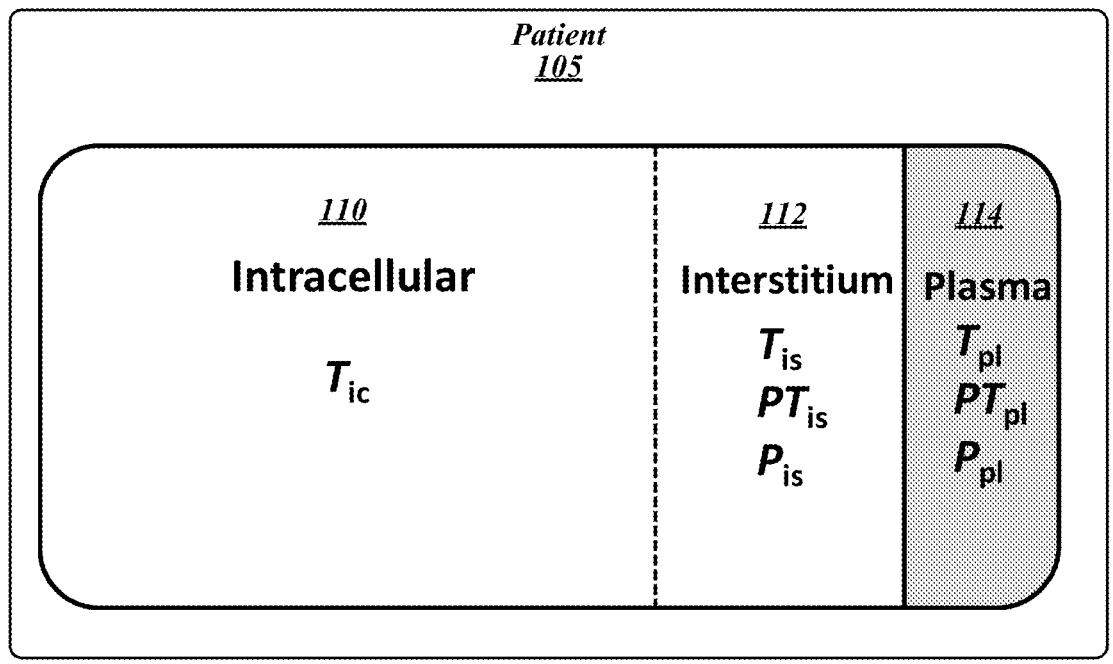
FIG. 1 illustrates a fluidic model of a patient.

The present embodiments will now be described more fully hereinafter with reference to the accompanying drawings, in which several exemplary embodiments are shown. The subject matter of the present disclosure, however, may be embodied in many different forms and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Various embodiments may generally be directed toward systems, methods, and/or apparatuses for performing displacement dialysis processes for removing protein-bound substances from patient blood. In general, a substance or target substance may be present within patient fluids in a free or unbound form and in a protein-bound form. FIG. 1 illustrates an example of a patient 105 depicting the patient fluids compartmentalized as intracellular fluid 110, interstitium fluid 112, and plasma fluid 114, where T indicates toxins and P indicates proteins. As shown in FIG. 1, free toxins ($T_{ic}$, $T_{is}$, and $T_{pl}$) may be equilibrated in intracellular fluid 110, interstitium fluid 112, and plasma fluid 114. Protein-bound substances or toxins ($PT_{is}$ and $PT_{pl}$) are distributed in the interstitium fluid 112 and plasma fluid 114 only. Conventional dialysis processes may be able to remove the substance in the unbound form, but not able (or at least not effectively and/or efficiently able) to remove the substance in the protein-bound form.

Some processes may introduce a displacer during dialysis treatment that is operative to displace the target substance from the protein in the protein-bound form to generate free substance. In general, a target substance is an unwanted substance for removal via dialysis that may be freed via application of a displacer. However, generating free target substances in the blood may cause the amount of substance to increase to unsafe levels. Accordingly, displacement dialysis processes according to some embodiments may operate to balance introducing a sufficient amount of the displacer to effectively generate free substance from protein-bound substance for removal via dialysis, while not causing an unsafe level of substance to be present in the blood during the treatment. For example, infusing the patient with an inadequate amount or concentration of the displacer may cause too much of the protein-bound substance to remain in the blood stream following dialysis treatment and/or may require a greatly increased dialysis treatment time to remove a sufficient amount of the substance. Alternatively, infusing the patient with too much of the displacer at a given time may cause the substance to reach unsafe concentrations in the blood, potentially causing harm to the patient. Accordingly, displacement dialysis processes according to some embodiments may include determining a displacer infusion process or profile operative to manage the infusion of displacer into the blood of a patient during dialysis to facilitate the effective removal of the substance while preventing the substance from reaching an unsafe level.

In some embodiments, substances may include foreign substances such as drug compounds. Non-limiting examples of drug compounds may include ibuprofen, valproic acid, phenytoin, carbamazepine, digoxin, and/or the like. In various embodiments, the protein that binds the substance may be or may include albumin. In exemplary embodiments, the displacer may be or may include aspirin. For example, drug compounds such as ibuprofen, valproic acid, phenytoin, carbamazepine, and/or digoxin bind to albumin, and aspirin binds to the same binding site on albumin. Accordingly, aspirin will compete for binding sites with the drug compounds, leading to increased free drug compounds and decreased (or even eliminated) protein-bound drug compounds. Although phenytoin, albumin, and aspirin are used in examples in this Detailed Description, embodiments are not so limited, as any substance, protein, and displacer combination(s) capable of operating according some embodiments are contemplated herein.

Dialysis processes may operate to minimize or even completely eliminate the end-dialysis toxic drug concentration in the minimum time possible, which may be achieved by maximizing the free drug concentration in serum or plasma. Increasing the free fraction of the substance may be achieved by infusing the displacer right before the dialysis interaction with patient blood (for instance, in the vicinity of where the blood engages a dialysis membrane). In this manner, displacer may compete more effectively for the binding protein and increase the free fraction of the substance. The patient should be undergoing dialysis or immediately undergo dialysis to reduce or even eliminate free substance diffusing to inaccessible fluid compartments of the patient fluidic system.

For example, a conventional non-displacement dialysis process may take about 360 to 420 minutes to take the concentration of a substance (for instance, phenytoin) from a toxic level (greater than 30 mg/L, such as about 70 mg/L) to a safe or therapeutic level (less than about 20 mg/L, such as about 15 mg/L). A displacement dialysis process may decrease this time to less than 100 minutes, such as about 75 minutes (for example, infusing a patient with 2000 mg aspirin dissolved in 200 ml saline before dialysis). The decrease in the time required to reach a safe or therapeutic level with a displacement dialysis process is due to the displacer significantly increasing the free substance concentration. However, the concentration of the free substance may spike during infusion of the displacer (for instance, the free concentration of phenytoin in the plasma may spike from about 10 mg/L to about 50 mg/L with 2000 mg aspirin dissolved in 200 ml saline before dialysis). It is the free concentration of the substance that may cause deleterious effects, such that pre-dialysis displacer infusion without displacer profiling according to some embodiments may actually harm the patient. Accordingly, some embodiments may provide displacer profile processes to avoid harmful spiking of substances, such as phenytoin.

In various embodiments, displacer profile processes may facilitate the infusion of displacer optimized to minimize or even eliminate the end-dialysis concentration of the target substance in a minimum time such that the free substance concentration does not go beyond or substantially beyond initial free concentration. Accordingly, displacement dialysis processes according to some embodiments may operate to provide a displacer infusion rate or profile such that the maximum concentration of the substance (for example, $T_{pl}$) at any time t during infusion and/or a dialysis treatment is less than (or substantially less than or equal to) the initial concentration of the substance ($T_0$) to provide the following infusion constraint: max $T_{pl}(t)<T_0$. The infusion constraint operates to protect the patient from harm due to a too high concentration of the free substance during the dialysis treatment due to generating free substance from protein-bound substance.

Figure 2:
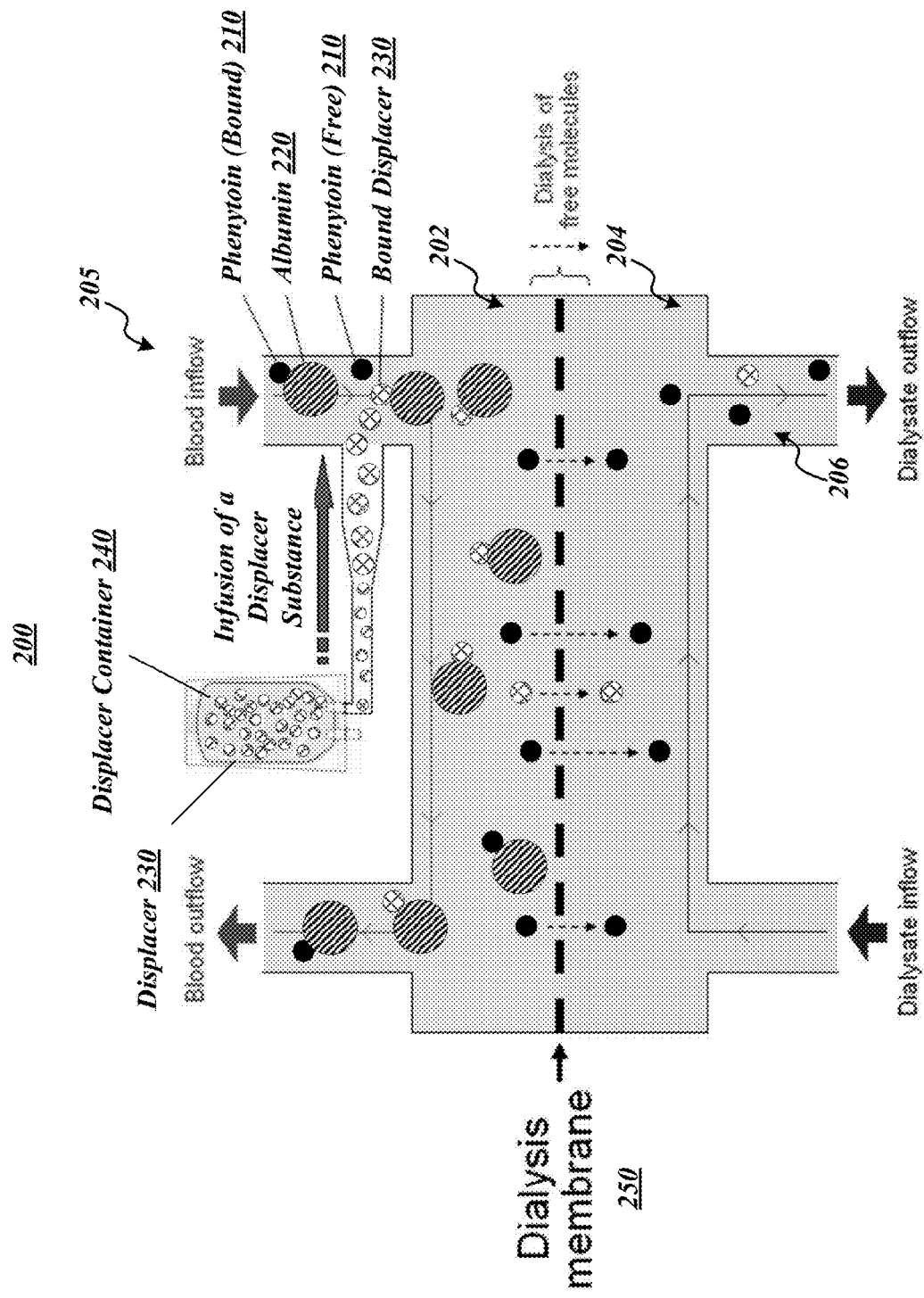
FIG. 2 illustrates an example of a first operating environment that may be representative of some embodiments of the present disclosure.

FIG. 2 illustrates an example of an operating environment 200 that may be representative of some embodiments. As depicted in FIG. 2, a dialysis machine 205 may operate to cause a dialysate inflow of a dialysis fluid 204 and a dialysis outflow of the dialysate fluid along with unwanted substances 206 (see, for example, FIGS. 8 and 9). Patient blood 202 may include a target substance in the form of phenytoin 210 bound to albumin 220 and free or unbound phenytoin 210. Unbound phenytoin 210 may cross a dialysis membrane 250 and be removed as an unwanted substance 206 with the dialysate outflow. Bound phenytoin 210 is not able to cross dialysis membrane 250 and, therefore, cannot be removed as an unwanted substance 206 with the dialysate outflow.

In some embodiments, dialysis machine 205 may include or may be in fluid communication with a displacer container 240 operative to facilitate the infusion of a displacer 230 into patient blood 202 via a patient blood inflow. As shown in FIG. 2, displacer 230 may compete for binding sites on albumin 220, leading to a decrease (or even an elimination) of bound phenytoin 210 and an increase in free phenytoin 210. An increase in free phenytoin 210 may facilitate the removal of, or removal of a greater amount of, phenytoin 210 from patient blood 202 than could be achieved in the absence of displacer 230.

The equilibrium association constant may be determined according to the following equation (1):

$$K_A = \frac{PT}{P \cdot T} = \frac{(1-f)T_{tot}}{(P_{tot} - (1-f)T_{tot}) \cdot fT_{tot}},$$

where P is protein concentration (for instance, albumin), T is toxin concentration (for instance, phenytoin), and f is the toxin free fraction. In general, 90% of phenytoin may be bound in therapeutic concentrations (for instance, 10-20 mg/L). Assuming a total albumin concentration of 650 μM (4.3 g/dL)), the equilibrium association constant may be about $1.5 \times 10^4$ M$^{-1}$.

Accordingly, displacer infusion processes according to some embodiments may involve two conflicting objectives: (1) minimize (or even eliminate) end-dialysis concentration of a target substance (for instance, phenytoin) in a minimum amount of time, and (2) enforce the infusion constraint to prevent harm to a patient. Accordingly, determining an infusion profile that satisfies (1) and (2) may involve a multi-objective optimization (MOO) process involving conflicting objectives ("displacement process MOO"). In some embodiments, a non-dominated sorting genetic algorithm (NSGA) may be used to solve a MOO. For example, NSGA II as described in Deb et al., "A Fast and Elitist Multiobjective Genetic Algorithm: NSGA-II," IEEE Transactions on Evolutionary Computation, vol. 6, no. 2, pp. 182-197, April 2002. Non-limiting examples of parameters that may be used for determining the infusion profile may include blood flow rate (Qb), dialysate flow rate (Qd), dialyzer size, patient size, and/or drug distribution volume (for instance, typically related to patient size).

Figure 3:
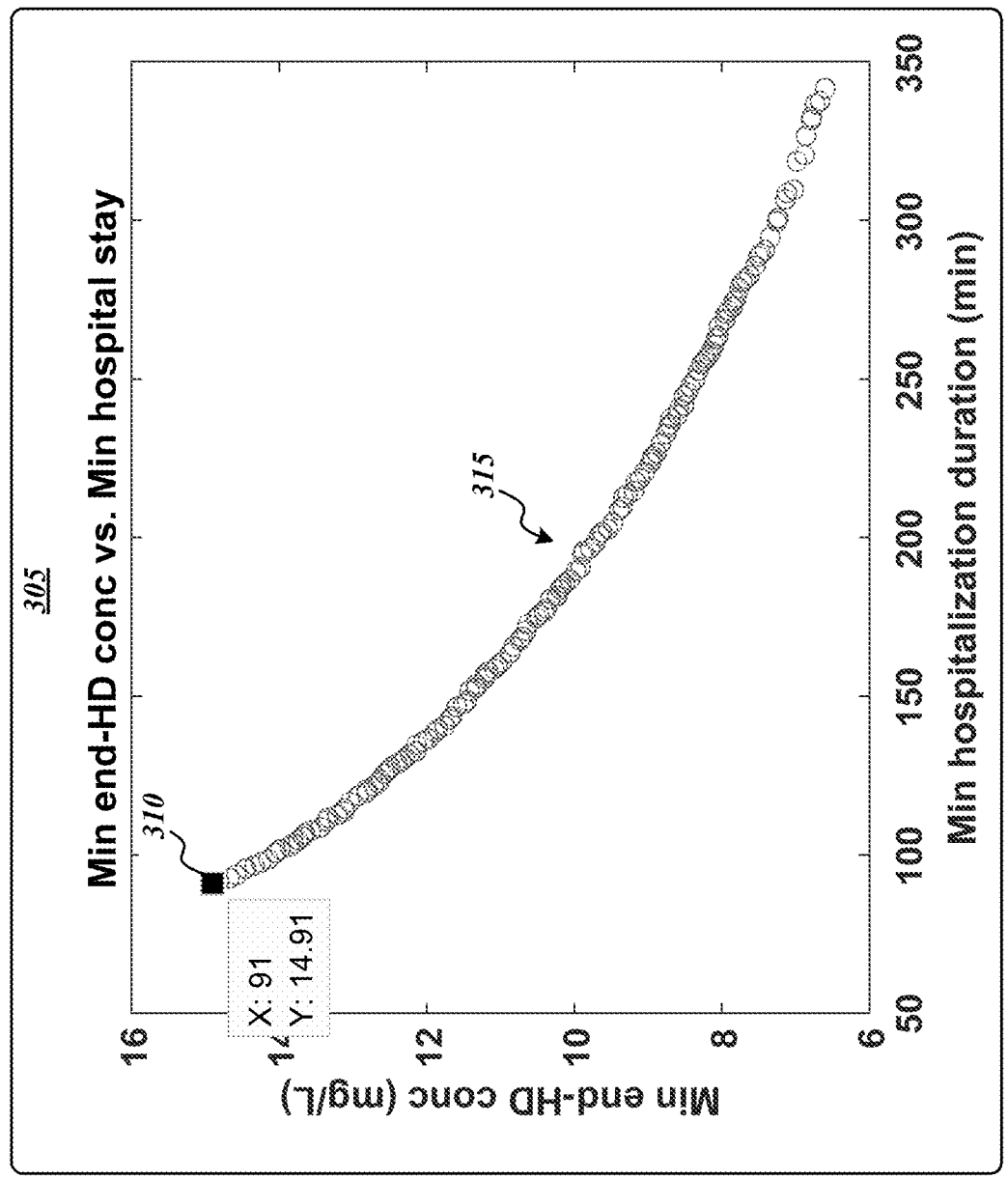
FIG. 3 illustrates an exemplary graph of multi-objective optimization (MOO) process solutions according to some embodiments of the present disclosure.

FIG. 3 depicts a graph 305 of competing NSGA-II solutions for the displacement process MOO. Plot 315 is a Pareto-optimal front of competing solutions to the displacement process MOO, with each point representing a choice between conflicting objectives. In various embodiments, a displacer infusion process may be determined, for example, as a point on the Pareto-optimal front 315. For example, point 310 may be selected because, among other things, the point may correspond to a vector of optimal decision variables resulting in a minimum possible dialysis time to provide a minimum possible end-dialysis target substance concentration within given constraints. Although a MOO process, such as NSGA-II, is used as an example for determining an optimal displacement infusion profile, embodiments are not so limited, as any process for determining an optimal displacement infusion profile capable of operating according to some embodiments is contemplated herein.

Figure 4:
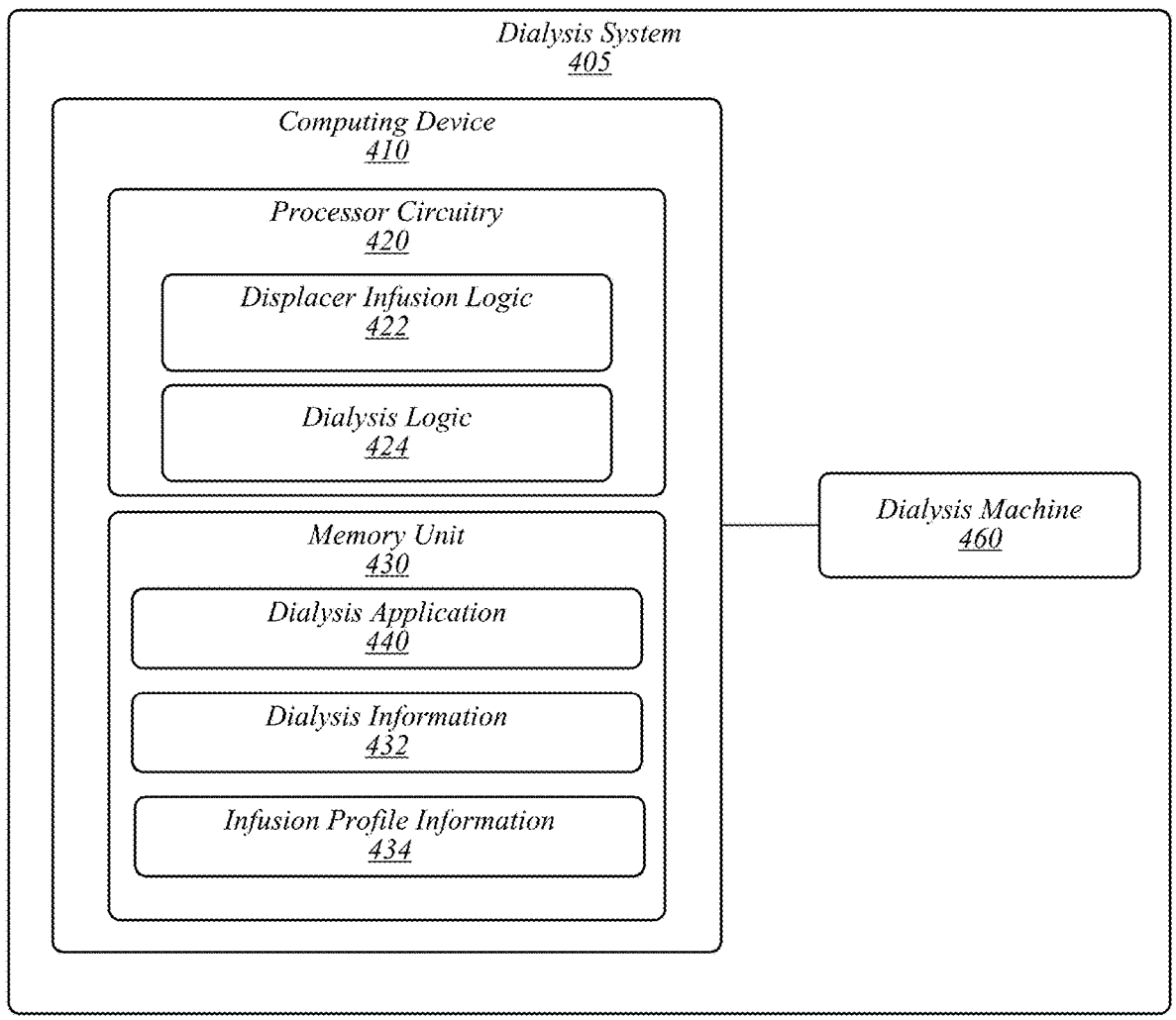
FIG. 4 illustrates an example of a second operating environment that may be representative of some embodiments of the present disclosure.

FIG. 4 illustrates an example of an operating environment 400 that may be representative of some embodiments. As shown in FIG. 4, operating environment 400 may include a dialysis system 405 associated with a dialysis machine 460 (for instance, see dialysis machine 205 of FIG. 2). In various embodiments, dialysis system 405 may include a computing device 410 communicatively coupled to dialysis machine 460. computing device 410 may be operative to manage, among other things, a dialysis process (for instance, a HD process) a displacer infusion process for dialysis machine 460.

Although only one computing device 410 and dialysis machine 460 are depicted in FIG. 4, embodiments are not so limited. In various embodiments, the functions, operations, configurations, data storage functions, applications, logic, and/or the like described with respect to the computing device 410 may be performed by and/or stored in one or more other computing devices (not shown), for example, coupled to computing device 410 via a network. A single computing device 410 and dialysis machine 200 are depicted for illustrative purposes only to simplify the figure. For example, computing device 410 may operate to partially or wholly operate a displacer infusion process and/or dialysis process for a plurality of dialysis machines 460 coupled to computing device 410, for instance, via a network. Embodiments are not limited in this context.

Computing device 410 may include a processor circuitry 420 communicatively coupled to a memory unit 430. Processing circuitry 420 may include and/or may access various logics for performing processes according to some embodiments. For instance, processor circuitry 420 may include and/or may access a displacer infusion logic 422 and/or a dialysis logic 424. Processing circuitry 420, displacer infusion logic 422, and/or dialysis logic 424, and/or portions thereof, may be implemented in hardware, software, or a combination thereof. As used in this application, the terms "logic," "component," "layer," "system," "circuitry," "decoder," "encoder," and/or "module" are intended to refer to a computer-related entity, either hardware, a combination of hardware and software, software, or software in execution, examples of which are provided by exemplary computing architecture 1000. For example, a logic, circuitry, or a module may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, combinations of any of the foregoing, and/or the like.

Although displacer infusion logic 422 and dialysis logic 424 are depicted in FIG. 4 as being within processor circuitry 420, embodiments are not so limited. For example, displacer infusion logic 422, dialysis logic 424, and/or any component thereof, may be located within an accelerator, a processor core, an interface, an individual processor die, implemented entirely as a software application (for instance, a dialysis application 440) and/or the like.

Memory unit 430 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, the memory unit 430 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 430 may store a dialysis application 440 that may operate, alone or in combination with the displacer infusion logic 422 and/or the dialysis logic 424, to control or otherwise manage various operational aspects of the dialysis machine 200. For example, displacer infusion logic 422 may operate to perform displacer infusion processes according to some embodiments. In another example, the dialysis logic 424 may operate to perform a dialysis process (for instance, an HD process) via dialysis machine 460.

In some embodiments, memory unit 430 may store dialysis information 432 that may include information required for dialysis application 440 to perform dialysis on a patient, including a displacer infusion process during a dialysis treatment. For example, dialysis information 432 may include patient physical information, dialysis treatment or prescription information, target substance information, binding protein information, displacer information, profile determination information, and/or the like. Embodiments are not limited in this context.

In various embodiments, profile determination information may include historical information (for example, associated with a patient, a dialysis treatment regimen, a target substance, a dialysis machine, and/or the like), information input via an operator, information automatically determined by dialysis application 440 or other operating entity of computing device 410, combinations thereof, and/or the like. In some embodiments, the historical information used to determine an infusion profile may include historical studies of target substance concentration during various flow rates of the displacer during a dialysis process. In some embodiments, the infusion profile may be based on monitoring of the concentration of the target substance (or another factor related to the concentration).

In various embodiments, profile determination information may include information that may be used to determine an infusion profile. For example, profile determination information may include a binding protein type, binding protein affinity, binding protein concentration, displacer type, target substance type, target dialysis time (for instance, minimum and maximum times), target concentration of the target substance at the end of dialysis), target substance concentration at the start of dialysis (for instance, at time $t_0$), estimations thereof, combinations thereof, and/or the like. Embodiments are not limited in this context.

In various embodiments, displacer infusion logic may determine at least one infusion profile (see, for example, FIG. 5) for a displacer over at least a portion of the duration of a dialysis treatment based on the profile determination information. In some embodiments, the infusion profile may be stored as infusion profile information 434 in memory unit 430. In various embodiments, dialysis application 440 (alone or in combination with displacer infusion logic 422) perform a dialysis treatment via dialysis machine that includes infusion of a displacer according to infusion profile information 434.

Figure 5:
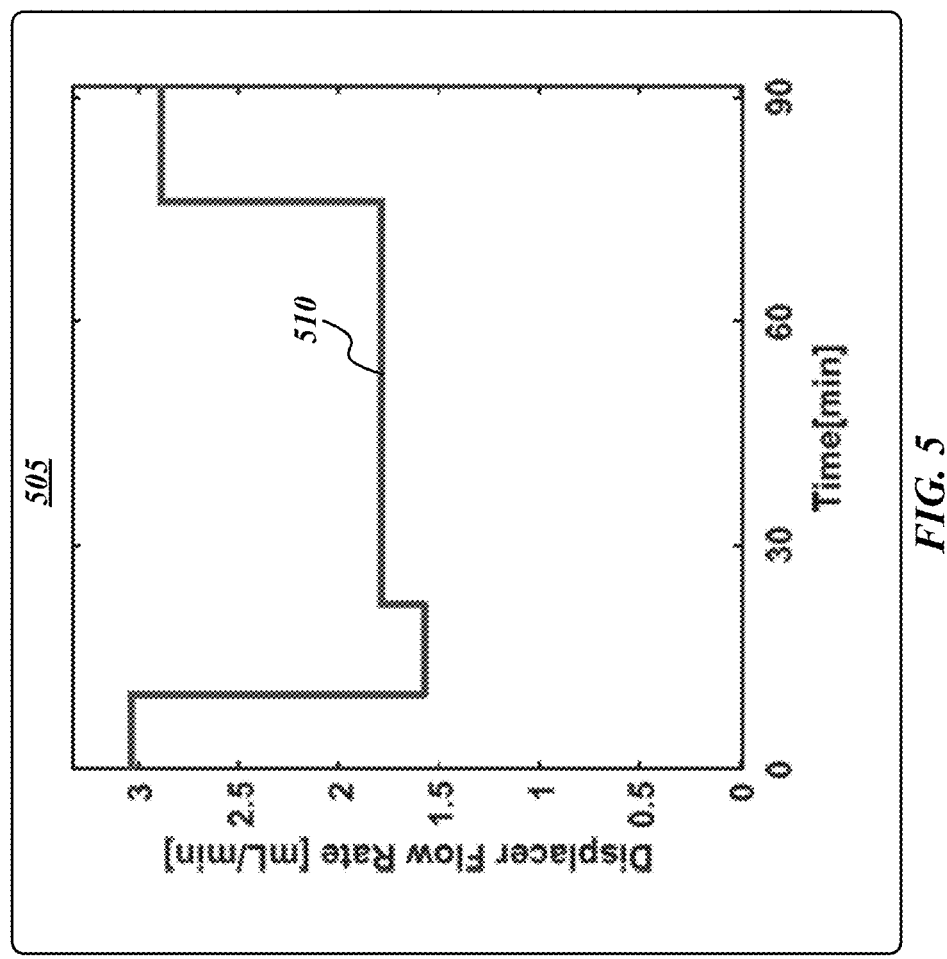
FIG. 5 illustrates an exemplary graph of an infusion profile according to some embodiments of the present disclosure.

FIG. 5 depicts a graph 505 of an infusion profile 510 generated according to some embodiments. As shown in FIG. 5, infusion profile 510 includes infusing a displacer (for instance, aspirin) at different flow rates (mL/min) over a period of time during at least a portion of a dialysis treatment. For instance, at time 90 min infusion may be complete with respect to the target substance, while the dialysis process may continue beyond 90 minutes. In another instance, the displacer infusion process may be active for an entirety or substantially an entirety of a dialysis process.

In the example of FIG. 5, the differential infusion of a displacer is managed via modifying a flow rate of the displacer (for example, at a constant concentration). In some embodiments, the amount of displacer infused into the patient may be changed by modifying the concentration of the displacer infused at a constant flow rate. Embodiments are not limited in this context.

Figure 6:
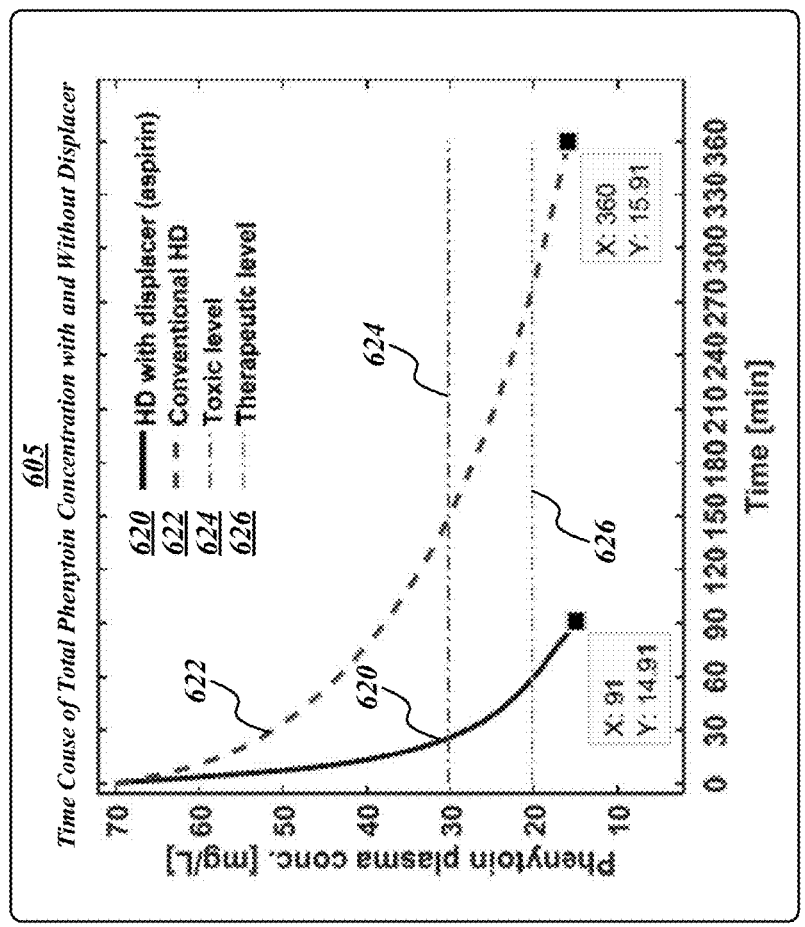
FIG. 6 illustrates exemplary graphs of target substance concentration during a plurality of dialysis processes according to the present disclosure.

FIG. 6 depicts a graph 605 of total target substance (i.e., phenytoin) concentration over time. Line 624 indicates a toxic level of phenytoin and line 626 indicates a therapeutic level (i.e., non-harmful) of phenytoin. Plot 622 depicts a conventional dialysis process without using a displacer, which required about 360 minutes to achieve a therapeutic level of phenytoin of about 16 mg/L starting at a concentration of about 70 mg/L of phenytoin. Plot 620 depicts a displacement dialysis processes according to some embodiments that includes a dialysis process (for instance, HD)

using a displacement infusion process according to various embodiments (for instance, according to profile 510 of FIG. 5), which only required about 90 minutes to achieve a therapeutic level of phenytoin of about 15 mg/L starting at a concentration of about 70 mg/L of phenytoin. As shown in plot 620, the displacement dialysis process using an infusion profile according to some embodiments meets the infusion constraint of not increasing the concentration of the target substance above the initial level at or around the start time (for instance, $t_0$) of dialysis.

Included herein are one or more logic flows representative of exemplary methodologies for performing novel aspects of the disclosed architecture. While, for purposes of simplicity of explanation, the one or more methodologies herein are shown and described as a series of acts, those skilled in the art will understand and appreciate that the methodologies are not limited by the order of acts. Some acts may, in accordance therewith, occur in a different order and/or concurrently with other acts from that shown and described herein. For example, those skilled in the art will understand and appreciate that a methodology could alternatively be represented as a series of interrelated states or events, such as in a state diagram. Moreover, not all acts illustrated in a methodology may be required for a novel implementation. Blocks designated with dotted lines may be optional blocks of a logic flow.

A logic flow may be implemented in software, firmware, hardware, or any combination thereof. In software and firmware embodiments, a logic flow may be implemented by computer executable instructions stored on a non-transitory computer readable medium or machine readable medium. The embodiments are not limited in this context.

Figure 7:
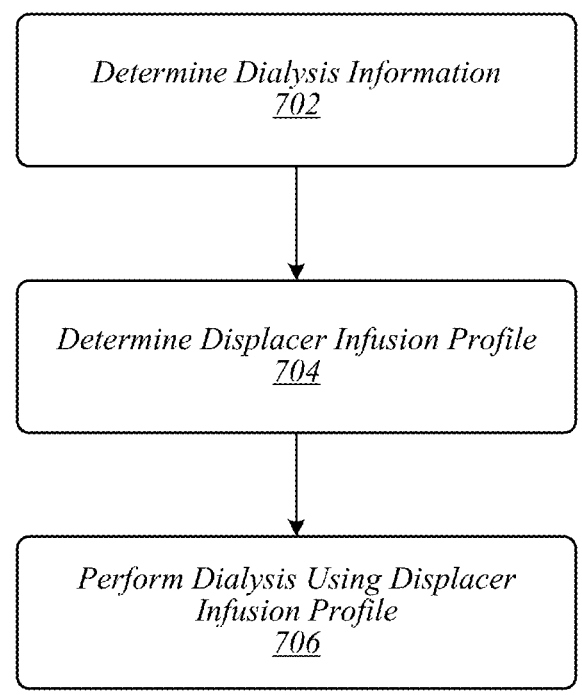
FIG. 7 illustrates a first logic flow in accordance with the present disclosure.

FIG. 7 illustrates an embodiment of a logic flow 700. The logic flow 700 may be representative of some or all of the operations executed by one or more embodiments described herein, such as dialysis machine 205 and/or processor circuitry 420, and/or components thereof. In some embodiments, the logic flow 700 may be representative of some or all of the operations of executing a displacer infusion process.

Logic flow 700 may determine dialysis information at block 702, as described above. For example, dialysis application 440 may determine dialysis information 432 associated with a dialysis treatment for a patient. In some embodiments, dialysis information 432 may include profile determination information that may be used to determine an infusion profile. In various embodiments, profile determination information may include historical information (for example, associated with a patient, a dialysis treatment regimen, a target substance, a dialysis machine, and/or the like), information input via an operator, information automatically determined by dialysis application 440 or other operating entity of computing device 410, combinations thereof, and/or the like. In some embodiments, the historical information used to determine an infusion profile may include historical studies of target substance concentration during various flow rates of the displacer during a dialysis process. In some embodiments, the infusion profile may be based on monitoring of the concentration of the target substance (or another factor related to the concentration).

At block 704, logic flow 700 may determine a displacer infusion profile. For example, dialysis application 440 (for instance, via displacer infusion logic 422) may determine a displacer infusion profile. In some embodiments, dialysis application 440 may determine a displacer infusion profile based at least in part on dialysis information, such as infusion determination information. In various embodiments, dialysis application 440 may determine a displacer infusion profile such that the maximum concentration of the substance (for example, $T_{pi}$) at any time t during infusion and/or a dialysis treatment is less than (or substantially less than or equal to) the initial concentration of the substance ($T_0$) to satisfy the following infusion constraint: max $T_{pi}(T)$ <$T_0$. In various embodiments, dialysis application 440 may determine a displacer infusion profile based on a MOO process, such as NSGA II.

Logic flow 700 may perform dialysis using the displacer infusion profile at block 706. For example, during a dialysis treatment, a displacer may be infused into the patient according to a displacer infusion profile, such as profile 510 of FIG. 5, to achieve a concentration profile the same or similar as plot 620 of FIG. 6.

Figure 8:
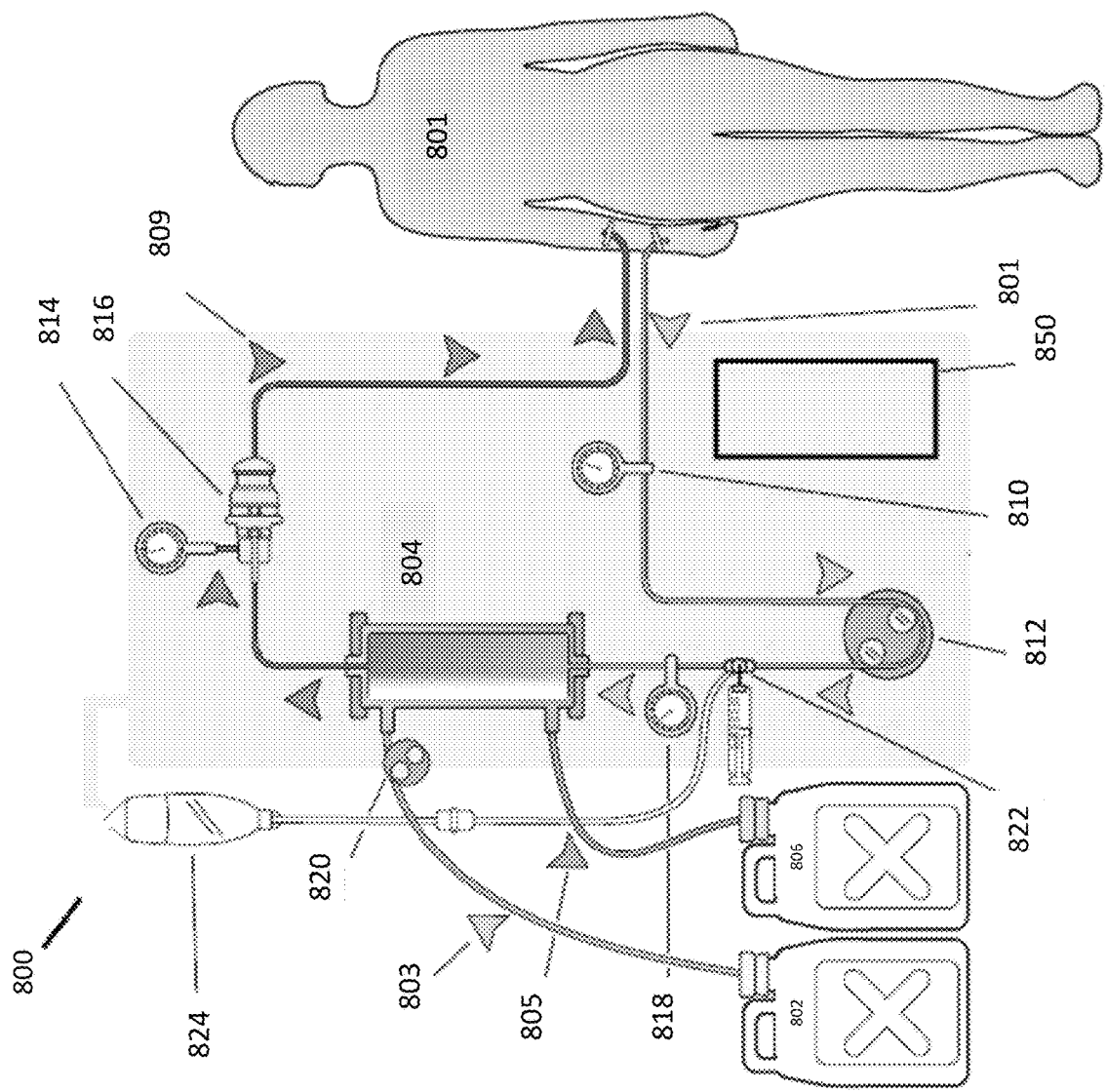
FIG. 8 illustrates an example hemodialysis system.

FIG. 8 illustrates a diagram of an exemplary embodiment of a dialysis system 800 in accordance with the present disclosure. Dialysis system 800 may be configured to provide hemodialysis (HD) treatment for a patient 801. Fluid reservoir 802 may deliver fresh dialysate to a dialyzer 804 via tubing 803, and reservoir 806 may receive spent dialysate once it has passed through dialyzer 804 via tubing 805. A hemodialysis operation may filter particulates and/or contaminates from a patient's blood through a patient external filtration device, for example, a dialyzer 804. As the dialysate is passed through dialyzer 804, unfiltered patient blood is also passed into dialyzer 804 via tubing 807 and filtered blood is returned to patient 801 via tubing 88809. Arterial pressure may be monitored via pressure sensor 810, inflow pressure monitored via sensor 818, and venous pressure monitored via pressure sensor 814. An air trap and detector 816 may ensure that air is not introduced into patient blood as it is filtered and returned to patient 801. The flow of blood and the flow of dialysate may be controlled via respective pumps, including a blood pump 88 and a fluid pump 820. Heparin 822, a blood thinner, may be used in conjunction with saline 824 to ensure blood clots do not form or occlude blood flow through the system.

In some embodiments, dialysis system 800 may include a controller 850, which may be similar to computing device 410 and/or components thereof (for instance, processor circuitry 420). Controller 850 may be configured to monitor fluid pressure readings to identify fluctuations indicative of patient parameters, such as heart rate and/or respiration rate. In some embodiments, a patient heart rate and/or respiration rate may be determinable by the fluid pressure in the fluid flow lines and fluid bags. Controller 850 may also be operatively connected to and/or communicate with additional sensors or sensor systems, devices, and/or the like, although controller 850 may use any of the data available on the patient's biologic functions or other patient parameters. For example, controller 850 may send patient data to computing device 410 to perform processes according to some embodiments.

Figure 9:
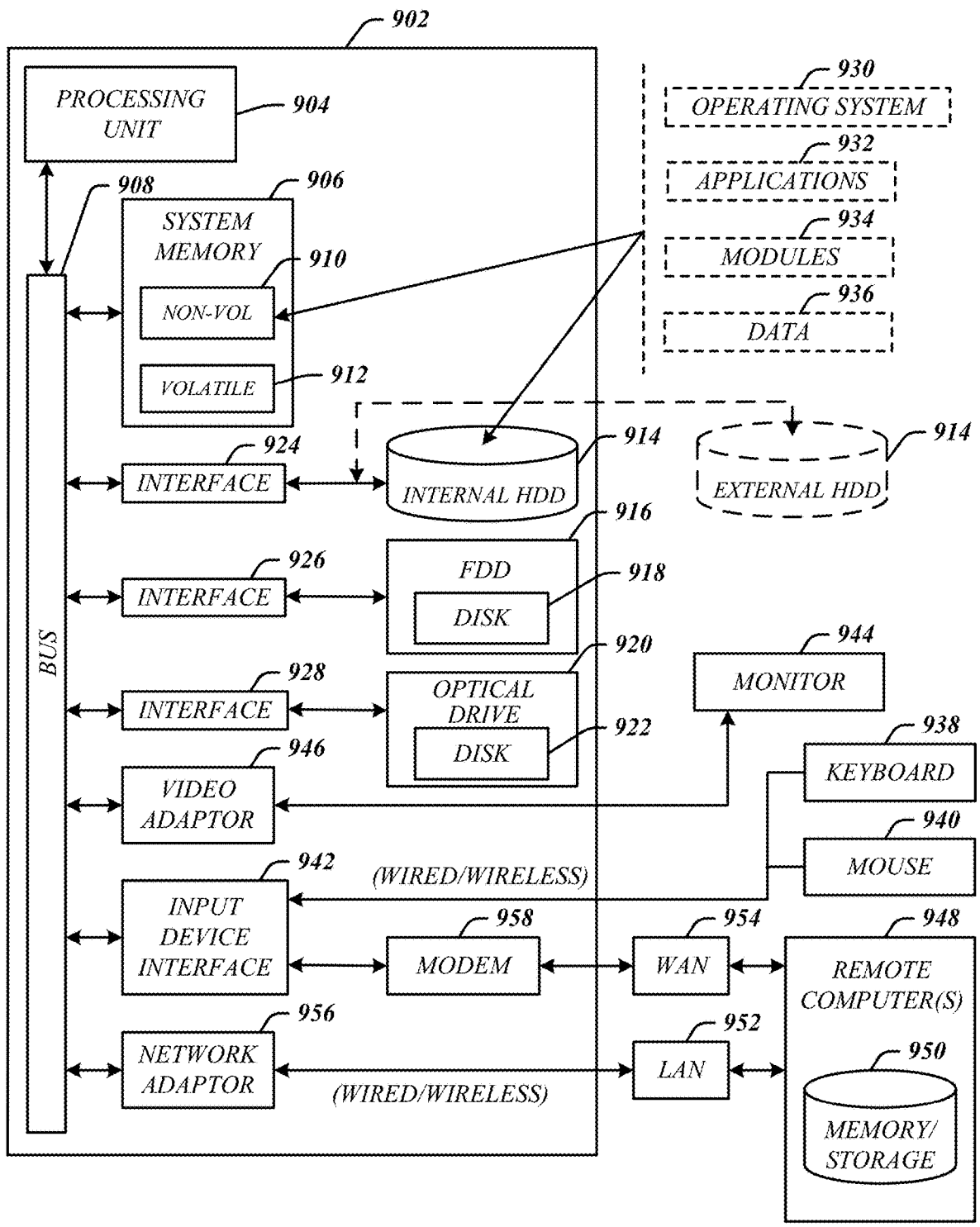
FIG. 9 illustrates an embodiment of a computing architecture according to the present disclosure.

FIG. 9 illustrates an embodiment of an exemplary computing architecture 900 suitable for implementing various embodiments as previously described. In various embodiments, the computing architecture 900 may comprise or be implemented as part of an electronic device. In some embodiments, the computing architecture 900 may be representative, for example, of computing device 902 and/or components thereof. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 900. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 900 includes various common computing elements, such as one or more processors, multi-core processors, co-processors, memory units, chip-sets, controllers, peripherals, interfaces, oscillators, timing devices, video cards, audio cards, multimedia input/output (I/O) components, power supplies, and so forth. The embodiments, however, are not limited to implementation by the computing architecture 900.

As shown in FIG. 9, the computing architecture 900 comprises a processing unit 904, a system memory 906 and a system bus 908. The processing unit 904 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 904.

The system bus 908 provides an interface for system components including, but not limited to, the system memory 906 to the processing unit 904. The system bus 908 can be any of several types of bus structure that may further interconnect to a memory bus (with or without a memory controller), a peripheral bus, and a local bus using any of a variety of commercially available bus architectures. Interface adapters may connect to the system bus 908 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 906 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 9, the system memory 906 can include non-volatile memory 910 and/or volatile memory 912. A basic input/output system (BIOS) can be stored in the non-volatile memory 910.

The computer 902 may include various types of computer-readable storage media in the form of one or more lower speed memory units, including an internal (or external) hard disk drive (HDD) 914, a magnetic floppy disk drive (FDD) 916 to read from or write to a removable magnetic disk 919, and an optical disk drive 920 to read from or write to a removable optical disk 922 (e.g., a CD-ROM or DVD). The HDD 914, FDD 916 and optical disk drive 920 can be connected to the system bus 908 by a HDD interface 924, an FDD interface 926 and an optical drive interface 929, respectively. The HDD interface 924 for external drive implementations can include at least one or both of Universal Serial Bus (USB) and IEEE 1384 interface technologies.

The drives and associated computer-readable media provide volatile and/or nonvolatile storage of data, data structures, computer-executable instructions, and so forth. For example, a number of program modules can be stored in the drives and memory units 910, 912, including an operating system 930, one or more application programs 932, other program modules 934, and program data 936. In one embodiment, the one or more application programs 932, other program modules 934, and program data 936 can include, for example, the various applications and/or components of computing device 49.

A user can enter commands and information into the computer 902 through one or more wire/wireless input devices, for example, a keyboard 938 and a pointing device, such as a mouse 940. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 904 through an input device interface 942 that is coupled to the system bus 908, but can be connected by other interfaces such as a parallel port, IEEE 994 serial port, a game port, a USB port, an IR interface, and so forth.

A monitor 944 or other type of display device is also connected to the system bus 908 via an interface, such as a video adaptor 946. The monitor 944 may be internal or external to the computer 902. In addition to the monitor 944, a computer typically includes other peripheral output devices, such as speakers, printers, and so forth.

The computer 902 may operate in a networked environment using logical connections via wire and/or wireless communications to one or more remote computers, such as a remote computer 949. The remote computer 949 can be a workstation, a server computer, a router, a personal computer, portable computer, microprocessor-based entertainment appliance, a peer device or other common network node, and typically includes many or all of the elements described relative to the computer 902, although, for purposes of brevity, only a memory/storage device 950 is illustrated. The logical connections depicted include wire/wireless connectivity to a local area network (LAN) 952 and/or larger networks, for example, a wide area network (WAN) 954. Such LAN and WAN networking environments are commonplace in offices and companies, and facilitate enterprise-wide computer networks, such as intranets, all of which may connect to a global communications network, for example, the Internet.

When used in a LAN networking environment, the computer 902 is connected to the LAN 952 through a wire and/or wireless communication network interface or adaptor 956. The adaptor 956 can facilitate wire and/or wireless communications to the LAN 952, which may also include a wireless access point disposed thereon for communicating with the wireless functionality of the adaptor 956.

When used in a WAN networking environment, the computer 902 can include a modem 959, or is connected to a communications server on the WAN 954, or has other means for establishing communications over the WAN 954, such as by way of the Internet. The modem 959, which can be internal or external and a wire and/or wireless device, connects to the system bus 908 via the input device interface 942. In a networked environment, program modules depicted relative to the computer 902, or portions thereof, can be stored in the remote memory/storage device 950. It will be appreciated that the network connections shown are exemplary and other means of establishing a communications link between the computers can be used.

The computer 902 is operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. An apparatus, comprising:
   at least one processor;
   a memory coupled to the at least one processor, the memory comprising instructions that, when executed by the at least one processor, cause the at least one processor to:
   access dialysis information for a dialysis process performed by a dialysis machine, the dialysis information indicating a target substance to be displaced from a binding compound by a displacer, and
   determine an infusion profile for infusing the displacer into a patient during a displacer infusion process of the dialysis process, the infusion profile determined based on the dialysis information and an infusion constraint.

2. The apparatus of claim 1, wherein the instructions, when executed by the at least one processor, cause the at least one processor to perform the displacer infusion process via the dialysis machine by infusing the patient with the displacer according to the infusion profile.

3. The apparatus of claim 1, the infusion constraint comprising maintaining a concentration of the target substance at or below an initial concentration during the displacer infusion process.

4. The apparatus of claim 1, the target substance comprising a drug compound and the binding compound comprising a protein.

5. The apparatus of claim 1, the target substance comprising phenytoin and the binding compound comprising albumin.

6. The apparatus of claim 5, the displacer comprising aspirin.

7. The apparatus of claim 1, wherein the instructions, when executed by the at least one processor, cause the at least one processor to determine the infusion profile based on a multi-objective optimization (MOO).

8. The apparatus of claim 7, the MOO determined based on a first objective of minimizing the target substance at a completion of the dialysis process in a minimum amount of time and a second objective comprising the infusion constraint, the infusion constraint comprising maintaining a concentration of the target substance at or below an initial concentration during the displacer infusion process.

9. The apparatus of claim 7, the MOO comprising a non-dominated sorting genetic algorithm (NSGA).

10. The apparatus of claim 1, the infusion profile comprising modifying a flow rate of the displacer into the patient over an infusion time period to satisfy the infusion constraint.

\* \* \* \* \*